United States Patent
Drzala et al.

(10) Patent No.: US 10,492,718 B2
(45) Date of Patent: Dec. 3, 2019

(54) APPARATUS FOR ASSESSING SKIN REACTIVITY TO A MATERIAL

(71) Applicants: Mark R. Drzala, Morristown, NJ (US); Mitchell F. Reiter, Bernardsville, NJ (US)

(72) Inventors: Mark R. Drzala, Morristown, NJ (US); Mitchell F. Reiter, Bernardsville, NJ (US)

( * ) Notice: Subject to any disclaimer, the term of this patent is extended or adjusted under 35 U.S.C. 154(b) by 0 days.

(21) Appl. No.: 15/948,620

(22) Filed: Apr. 9, 2018

(65) Prior Publication Data

US 2019/0307389 A1    Oct. 10, 2019

(51) Int. Cl.
*A61B 5/00* (2006.01)
*G01N 33/483* (2006.01)

(52) U.S. Cl.
CPC .............. *A61B 5/411* (2013.01); *A61B 5/445* (2013.01); *A61B 5/681* (2013.01); *G01N 33/4833* (2013.01)

(58) Field of Classification Search
None
See application file for complete search history.

(56) References Cited

U.S. PATENT DOCUMENTS

| | | | |
|---|---|---|---|
| 3,212,495 A | 10/1965 | Osbourn et al. | |
| 3,515,126 A | 6/1970 | Fregert | |
| 3,597,976 A * | 8/1971 | Fryar | A61B 5/6833 116/219 |
| 3,602,137 A * | 8/1971 | Fort Camp | B41J 1/30 101/29 |
| 4,031,348 A * | 6/1977 | Eberhardt | G04C 3/001 200/530 |
| 4,205,689 A | 6/1980 | Brennan | |
| 4,836,217 A | 6/1989 | Fischer | |
| 4,904,448 A * | 2/1990 | Kawahara | A61B 5/00 422/420 |
| 5,342,317 A * | 8/1994 | Claywell | A61B 5/00 128/DIG. 26 |
| 5,392,261 A * | 2/1995 | Hsu | G04B 37/1413 368/281 |
| 5,546,955 A * | 8/1996 | Wilk | A61B 5/015 600/549 |
| 7,052,472 B1 * | 5/2006 | Miller | A61B 5/01 600/549 |

(Continued)

FOREIGN PATENT DOCUMENTS

DE    20103540 US    *    5/2001
FR    3040868 A1         3/2017

OTHER PUBLICATIONS

Starr, O. et al., "Patch Testing for Contact Dermatitis" published online at https://patient.info/skin-conditions/contact-dermatitis/patch-testing-for-contact-dermatitis printed Jun. 25, 2019.

*Primary Examiner* — Matthew Kremer
(74) *Attorney, Agent, or Firm* — Fox Rothschild LLP

(57) ABSTRACT

An apparatus including a wearable holder and a test material unit and a method for assessing skin reactivity to a test material are disclosed. The wearable holder is configured to hold the test material against the wearer's skin over a period of time to allow for an assessment of skin reactivity to the test material. The apparatus is provided to meet the needs of different patient populations.

16 Claims, 3 Drawing Sheets

(56) References Cited

U.S. PATENT DOCUMENTS

| | | | |
|---|---|---|---|
| 9,028,407 B1* | 5/2015 | Bennett-Guerrero | ........................ A61B 5/1121 600/301 |
| 9,918,541 B2* | 3/2018 | Byun | ........................ A45F 5/02 |
| 2004/0057983 A1 | 3/2004 | Schmidt | |
| 2004/0087314 A1* | 5/2004 | Duncan | .................. G01C 21/00 455/456.1 |
| 2006/0042139 A1* | 3/2006 | Mendes | .................. G09F 3/005 40/633 |
| 2008/0097221 A1* | 4/2008 | Florian | .............. A61B 5/02433 600/476 |
| 2008/0252902 A1* | 10/2008 | Oya | ........................ F16J 9/14 356/614 |
| 2010/0100005 A1* | 4/2010 | Mir | ........................ A61B 5/411 600/556 |
| 2011/0112405 A1* | 5/2011 | Barthe | .................. A45D 44/005 600/459 |
| 2011/0264003 A1* | 10/2011 | Hamann | ............ A61B 10/0035 600/556 |
| 2011/0306898 A1 | 12/2011 | Stierstorfer | |
| 2016/0299093 A1 | 10/2016 | Gilbert | |
| 2017/0007170 A1* | 1/2017 | Smith | ..................... A61B 5/411 |

* cited by examiner

APPARATUS FOR ASSESSING SKIN REACTIVITY TO A MATERIAL

FIELD OF THE INVENTION

The present invention relates generally to an apparatus for assessing skin reactivity to a material and more specifically relates to an apparatus for assessing skin reactivity to medical implant materials.

BACKGROUND OF THE INVENTION

Many people report a history of hypersensitivity to metals such as those found in costume jewelry, belt buckles, and watches. Medical studies now show that some people are also hypersensitive to the metals used in various surgical implants such as hip and knee replacements. Determining if someone is hypersensitive to specific implant materials would provide very useful information to patients who are considering implant surgery or who may already have undergone such a procedure.

Presently, persons who suspect that they are sensitive to metals are typically referred for skin patch-testing under the care of a dermatologist for confirmation. Another less common option available to test for hypersensitivity to metals is a blood test called a lymphocyte transformation test. Both types of testing are typically ordered by a physician (typically an allergist), are time-consuming, costly, and are not performed routinely. Additionally, it remains unknown which patients need to undergo evaluation, and there is no defined standard for determining what constitutes a positive test for potential hypersensitivity to various metals. There are currently no over-the-counter kits or devices that allow patients to undergo some form of preliminary assessment to test for cutaneous hypersensitivity to topically applied metals.

The present disclosure aims to provide a non-invasive, reliable, convenient, and inexpensive method of detecting the presence of skin reactivity to materials, such as medical implant materials.

SUMMARY OF THE INVENTION

An apparatus for assessing skin reactivity to a material is disclosed. The apparatus includes a holder and a test material unit. The holder further includes a test portion and a holding portion. The test portion includes a concave housing compartment adapted to receive and contact the test material unit therein. The periphery of the test material unit substantially matches the shape of the inner surface of the concave housing compartment. The holding portion is configured to cause the test material unit to have direct contact with the skin of the subject. The test material unit includes a test material and is removably mounted to the concave housing compartment of the test portion of the holder.

In an embodiment, the holder is formed of an inert and hypoallergenic material. The holding portion of the holder is a bracelet, a band, a wristband, a chest band, a leg band, a necklace, an anklet, a belt, a waist belt, a ring, an earring, or a watch-band style holder. In one embodiment, the holding portion of the holder is an elastic band. In some embodiments, the holding portion of the holder further comprises a fastening means. In one embodiment, the holding portion of the holder further is adjustable or stretchable. The fastening means of the holding portion can be a hook-and-loop, a buckle closure or a post-hole structure.

In some embodiments, the test material is an orthopedic surgery metal. The orthopedic surgery metal includes aluminum, vanadium, chromium, cobalt, molybdenum, nickel, and titanium. The orthopedic surgery metal may also include a metal alloy, for example, a titanium alloy (e.g., Ti6Al-4V has 90% titanium, 6% aluminum, and 4% vanadium, 0.25% iron and 0.2% oxygen). In some embodiments, the test material is a non-metallic orthopedic surgery material. The non-metallic orthopedic surgery material includes polymethyl methacrylate, polyethylene, polyaryl ether ketone (e.g., polyether ether ketone), and carbon fiber. In some embodiments, the test material is a dental implant material including titanium, zirconium, aluminum, and vanadium or a dental amalgam consisting essentially of liquid mercury and a metal alloy mixture having mercury, silver, tin, copper, or combinations of two or more thereof. In some embodiments, the test material may include a metal salt. In some embodiments, the test material may further include an inert carrier on which the metal salt can be placed.

In some embodiments, the test material unit includes an identification on a surface of the test material unit. The identification indicates a test material type, a manufacture date, a serial code, a medical provider name, or a combination of two or more thereof. In some embodiments, the identification is embossed on the surface of the test material unit.

In some embodiments, the test material unit comprises a first test material and a second test material, the first test material and the second test material being jointly attached against each other, such that the first test material and the second test material respectively occupy the opposing portions of the test material unit and only the first test material or the second test material makes direct contact with the skin of the subject. In some embodiments, the first test material and the second test material are removably attached to each other, such that one or more combinations of test materials are assembled for a single test material unit.

In another aspect of the disclosure, a kit for assessing skin reactivity to a material is also presented. The kit includes one or more holders and one or more test material units described above.

In yet another aspect of the disclosure, a method for assessing skin reactivity to a material is provided. The method includes applying the apparatus as described above on the skin of the subject, such that the test material unit of the apparatus makes direct contact with the skin for a predetermined period of time. The method further includes determining the presence of skin reactivity based on one or more cutaneous reactions of the skin with direct contact with the test material unit of the apparatus.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings, the like reference characters refer to the same parts throughout the different views. The drawings depict only typical embodiments of the present disclosure and, therefore, are not to be considered limiting in scope.

DETAILED DESCRIPTION OF THE INVENTION

Figure 1:
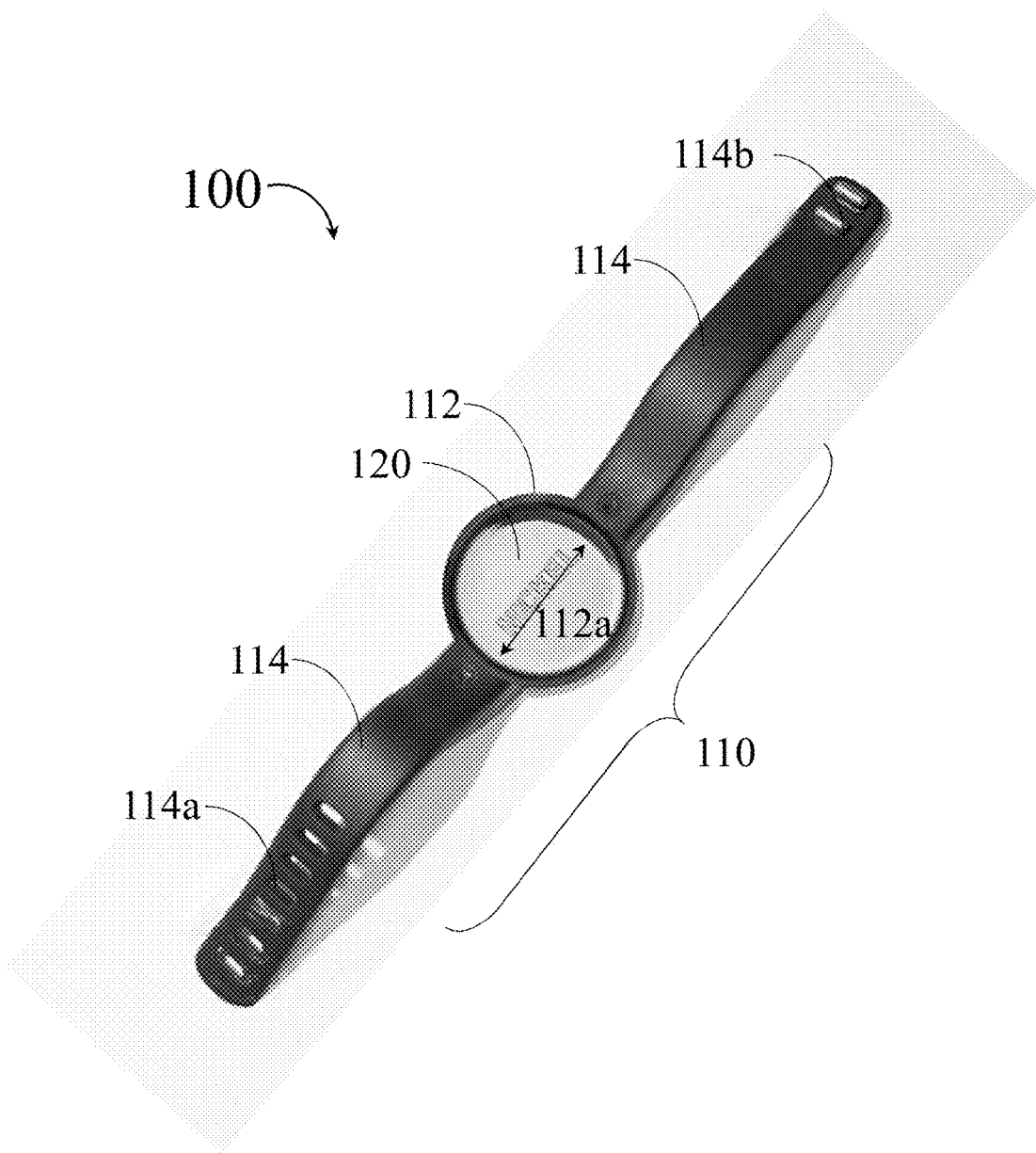
FIG. 1 depicts an example of an apparatus for assessing skin reactivity to a material which contains a wristband-style holder.

This disclosure is not limited to the particular systems, methodologies or protocols described, as these may vary. The terminology used in this description is to describe the particular versions or embodiments only and is not intended to limit the scope.

The advent of orthopedic and other medical implants has transformed the treatment of bone and joint disorders as well as other medical conditions by improving quality of life, increasing mobility, and reducing pain in affected patients. Most implants used in reconstructive surgical procedures are composed of metal alloys that contain classic contact allergens such as nickel, cobalt, and chromium. Extensive medical literature now exists describing patients experiencing hypersensitivity reactions to implant materials following their surgical procedures. Potential allergic complications after implantation of orthopedic metal devices include cutaneous eruptions, chronic joint pain, edema, implant loosening, and joint failure. In some cases, this has led to the need for additional surgery to remove the implant containing the offending material.

Despite the fact that allergies are on the rise in the western world, testing patients prior to surgical procedures involving implants is not routinely performed. The current testing techniques are not easy to interpret and typically involve referral to a dermatologist for skin testing. It has been proposed that previous cutaneous reaction to worn metals is an excellent predictor of metallic hypersensitivity. Since many reconstructive surgeries can be performed using implants of different metallic compositions, knowing about a patient's hypersensitivities can allow for modification of the procedure to avoid implants that contain the specific metals to which the patient is hypersensitive.

To address this need, the present disclosure provides an apparatus for assessing skin reactivity to a material. The disclosed apparatus can be adapted to meet the specific needs of dentists, surgeons, and/or other physicians to help provide information that could assist in determining which patients may require referral to specialists (i.e., allergists) for more extensive testing. The information gained may also help dentists and surgeons determine more appropriate treatments and may assist them in choosing safer implants, for example, avoiding the use of dental amalgam and certain metals in potentially hypersensitive individuals.

The apparatus includes a holder and a test material unit. The holder is configured to be worn on a body part of a wearer, such as ankles, fingers, neck, etc. The holder further includes a test portion and a holding portion. The test portion includes a concave housing compartment adapted to receive and contact the test material unit therein. The periphery of the test material unit substantially matches the shape of the inner surface of the concave housing compartment. The holding portion is configured to cause the test material unit to have direct contact with the skin of the subject. The test material unit includes a test material and is removably mounted to the concave housing compartment of the test portion of the holder.

The shape of the inner surface of the concave housing compartment of the holder may include, without limitation, circular, elliptical, square, rectangular, and polygonal, quadrilateral, square, triangular, parallelogram, pentagonal, hexagonal, heptagonal and octagonal. For example, the holder illustrated in FIG. 1 contains a concave housing compartment having a circular inner surface. Likewise, the shape of the test material unit may include, without limitation, circular, elliptical, square, rectangular, and polygonal, quadrilateral, square, triangular, parallelogram, pentagonal, hexagonal, heptagonal and octagonal, such that the shape of the inner surface of the concave housing compartment of the holder substantially matches that of the test material unit. For example, the test material units illustrated in FIG. 1 and FIG. 2 have a circular shape.

The holder can be a wearable bracelet or any other wearable articles. Examples of wearable articles include, without limitation, a bracelet, a band, a wristband, a pendant, a chest band, a leg band, a necklace, an anklet, a belt, a waist belt, a ring, an earring, and a watch-band style holder. For example, a band for testing an implant material can be adapted to be worn on various body parts (e.g., wrists, ankles, elbows, knees, neck, fingers, and toes).

In one embodiment, the holding portion of the holder is an elastic band. In some embodiments, the holding portion of the holder further includes a fastening means. In some embodiments, the holding portion of the holder further is adjustable or stretchable, allowing for the material being tested to be firmly held and secured against the subject's skin.

Figure 3:
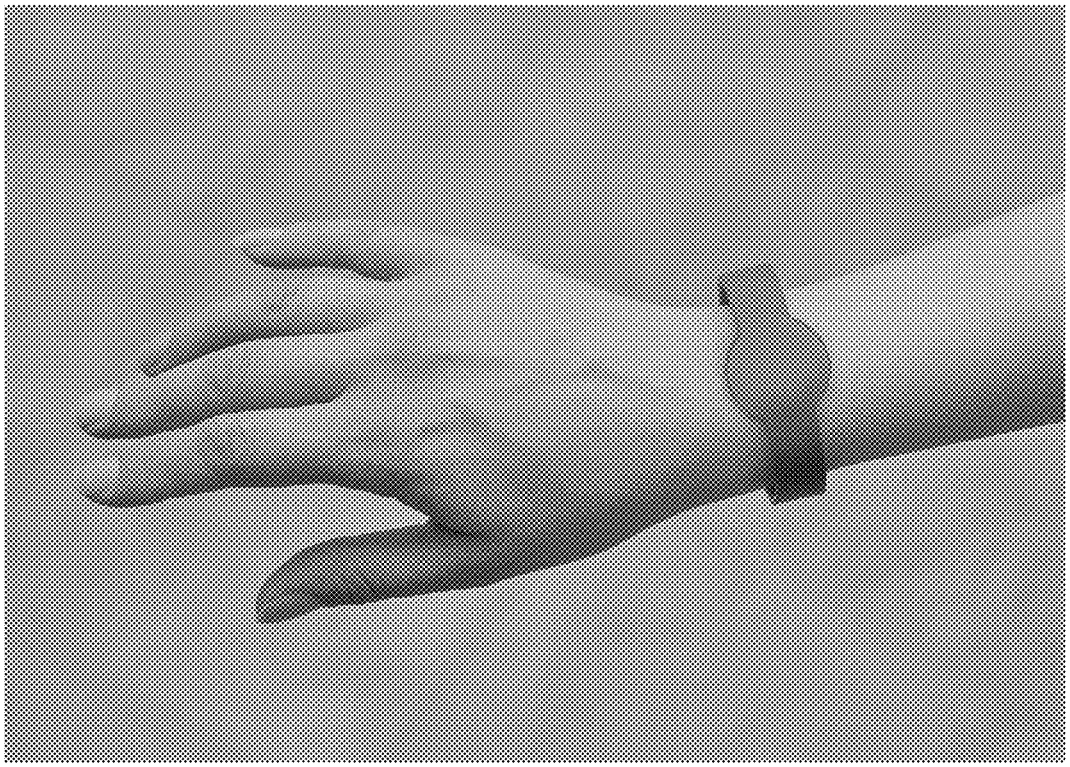
FIG. 3 shows an example of an apparatus with a wristband-style holder worn around the wrist of a subject.

Referring to FIG. 1, an exemplary apparatus 100 for assessing skin reactivity to a test material is illustrated. The apparatus 100 contains a wristband-style holder 110 and a test material unit 120. The holder 110 further includes a test portion 112 and a holding portion 114. The test portion 112 includes a concave housing compartment 112a adapted to receive and contact the test material unit 120 therein. The periphery of the test material unit 120 substantially matches the shape of the inner surface of the concave housing compartment 112a. The holding portion 114 is configured to cause the test material unit 120 to have direct contact with the skin of the subject. The test material unit 120 includes a test material and is removably mounted to the concave housing compartment 112a of the test portion 112 of the holder 110. The holding portion 114 of the holder 110 may further include one or more fastening means 114a and 114b. The fastening means 114a and 114b of the holding portion 114 can be a hook-and-loop or a buckle closure or a post-hole structure. For example, the fastening means 114a may include one or more holes, and the fastening means 114b may include one or more molded posts. The free strap ends of the holding portion 114 of the holder 110 can be adjustably secured together by mating the one or more holes of the fastening means 114a and the one or more molded posts of the fastening means 114b. An exemplary apparatus worn by a subject is shown in FIG. 3.

In an embodiment, the holder is made of a hypoallergenic, inert, or latex-free material (i.e., silicone), suitable for holding specific metals or other commonly used medical implant materials in direct contact with the subject's skin. The material to be tested can be worn using the holder in direct contact with the skin for several days. A cutaneous reaction to the applied material could suggest potential hypersensitivity.

Cutaneous skin reactions induced by exposure to the implant material may include, but would not be limited to, the following: red rash, swelling, erythema, eczema, pruritis, burning, urticaria (hives), painful angioedema, blisters, and wheals (welts). These reactions may not appear until 24-72 hours after exposure to the allergen. Those patients eliciting positive skin reactions would be advised to seek out further formal medical evaluation and care with their surgeon, primary care physician, or an appropriate medical specialist (likely a dermatologist or allergist). This information could help direct dentists and surgeons to customize treatment to avoid implants and medical materials that could cause hypersensitivity and lead to complications and adverse sequelae.

The test material unit can be fitted and secured in the concave housing compartment of the test portion of the holder by one or more fastening means. In one example, the concave housing compartment may have a slightly smaller size than the test material unit, such that the test material unit can be fitted and secured in the concave housing compartment with the help of elasticity of the material constituting the holder. In another example, the test material unit can be secured in the concave housing compartment by using a snap-fit mechanism. In yet another example, the inner surface of the concave housing compartment may include an internal thread, and the test material unit may include an external thread. The external thread of the test material unit is configured to be received by the internal thread of the concave housing compartment, whereby the test material unit is rotationally fitted and secured in the concave housing compartment. Alternatively and/or additionally, the test material unit can be secured by one or more fasteners (e.g., screws) or adhesive (e.g., glue). In some embodiments, the holder and the test material unit may be fabricated as a single piece.

The test material unit can include any test materials subjected to a skin hypersensitivity test. The test materials may include implant materials commonly used in medicine and dentistry or implant materials that are specific to the needs of certain patient populations. For example, the test materials can include metals commonly used in orthopedic fracture fixation and joint replacement procedures including, without limitation, aluminum, chromium, cobalt, molybdenum, nickel, and titanium, or other identified implant materials.

In another example, the test materials can include non-metallic materials frequently used in orthopedic surgery including, without limitation, polymethyl methacrylate (PMMA or bone cement), polyethylene (joint replacement liners), polyaryl ether ketone (e.g., PEEK), and carbon fiber. In yet another example, the test materials can include a dental amalgam—a liquid mercury and metal alloy mixture including, without limitation, mercury, silver, tin, copper, and other trace metals, and combinations of two or more thereof. Dental implants may also include, without limitation, titanium, zirconium, aluminum, and vanadium. Examples of other test materials include, without limitation, palladium, manganese, iron, latex, styrax (found in medical adhesives Mastisol and Tincture of Benzoin), balsam of Peru, gum mastic (in Mastisol), and gutta-percha (implanted in teeth after root canals). In some embodiments, the test material may include a metal salt. In some embodiments, the test material may further include an inert carrier on which the metal salt can be placed.

In some embodiments, the test material unit includes an identification on a surface of the test material unit. The identification indicates a test material type, a manufacture date, a serial code, a medical provider name, or a combination of two or more thereof. The identification can also use different colors or shapes to distinguish the material being tested from each other. In some embodiments, the identification is embossed on the surface of the test material unit.

Figure 2:
FIG. 2 depicts an example of a test material unit mountable to the holder as illustrated in FIG. 1.

Referring to FIG. 2, an example of a test material unit 120 is illustrated. The test material unit 120 includes nickel as a test material. The test material unit contains a top surface 121 and a bottom surface 122. The top surface 121 may have a different or the same size as compared to the bottom surface 122. In one example, the top surface 121 may have a smaller size than the bottom surface 122, as shown in FIG. 2. The smaller top surface 121 is removably received by the housing compartment 112a of the holder 110 (see FIG. 1), and the bottom surface 122 makes direct contact with the skin of a wearer. The top surface 121 can further include an identification 123 (e.g., "NICKEL" mark) embossed thereon indicating a test material type (e.g., nickel), a manufacture date, a serial code, a medical provider name, or a combination of two or more thereof.

In some embodiments, the test material unit comprises a first test material and a second test material, the first test material and the second test material being jointly attached against each other, such that the first test material and the second test material respectively occupy the opposing portions of the test material unit and only the first test material or the second test material makes direct contact with the skin of the subject. In some embodiments, the first test material and the second test material are different materials. In some embodiments, the first test material and the second test material are removably attached to each other, such that one or more combinations of test materials are assembled for a single test material unit.

The present disclosure also provides a method for assessing skin reactivity to a material is provided. The method includes applying the apparatus as described above on the skin of the subject, such that the test material unit of the apparatus makes direct contact with the skin for a predetermined period of time. The method further includes determining the presence of skin reactivity based on one or more cutaneous reactions of the skin with direct contact with the test material unit of the apparatus.

Surgical procedures involving metallic implants are increasingly common. In the United States alone, more than 1 million lower extremity total joint replacements are performed each year. In addition, three million Americans have dental implants, and that number has been increasing by 500,000 per year. Some of these patients go on to experience adverse events related to their implants due to hypersensitivity to the implanted metal.

The results of scientific studies suggest a role for skin patch-testing before inserting a surgical implant in patients who report a history of metal hypersensitivity. It is important to note that many patients who prove to be hypersensitive to the metallic implants do not have a history of previous hypersensitivity to metal jewelry. This implies that potentially all patients could benefit from metallic hypersensitivity testing and this is currently only available through costly formal dermatologist evaluation and follow up.

A widely available and economical implant material skin hypersensitivity testing kit could allow for early screening of patients scheduled to undergo implant surgeries. The result of this skin sensitivity testing could be used to help provide interested individuals with preliminary information with regards to potential metal hypersensitivities. These individuals could then be directed to medical specialists who could then provide a more definitive diagnosis. It would be left to the treating physician to determine which patients will then need a formal referral to an allergist. This device could provide important preliminary information at a reasonable cost that may assist in the determination as to which patients require more focused testing.

The use of the word "a" or "an", when used in conjunction with the term "comprising" in the claims and/or the specification, may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

What is claimed is:

1. An apparatus for assessing skin reactivity to a test material, comprising:
   a holder and
   a test material unit,
   wherein the holder further comprises a test portion and a holding portion,
   wherein the holder is formed of an inert and hypoallergenic material;
   wherein the test portion comprises a concaved housing compartment with an opening in a down orientation and a closed end in an up orientation,
   wherein the concaved housing compartment is adapted to receive and contact the test material unit therein,
   wherein a periphery of the test material unit matches a shape of an inner surface of the concaved housing compartment,
   wherein the concaved housing compartment is closed at the closed end so as to conceal a top surface of the test material unit;
   wherein the holding portion is configured to cause a bottom surface of the test material unit to have direct contact with a skin of a subject;
   wherein the test material unit consists of an implantable medical metal or alloy and is mounted to the concaved housing compartment of the test portion of the holder, and
   wherein the apparatus is configured to be worn for a plurality of days and configured to be removed and reattached.

2. The apparatus according to claim 1, wherein the holding portion of the holder is selected from the group consisting of a bracelet, a band, a wristband, a chest band, a leg band, an anklet, a belt, a waist belt, and a watch-band style holder.

3. The apparatus according to claim 1, wherein the shape of the inner surface of the concaved housing compartment is circular, elliptical, square, rectangular, polygonal, quadrilateral, triangular, parallelogram, pentagonal, hexagonal, heptagonal or octagonal.

4. The apparatus according to claim 1, wherein the holding portion of the holder is an elastic band.

5. The apparatus according to claim 1, wherein the holding portion of the holder is adjustable or stretchable.

6. The apparatus according to claim 1, wherein the holding portion of the holder further comprises a fastening means.

7. The apparatus according to claim 6, wherein the fastening means of the holding portion is a hook-and-loop, a button closure, or a buckle closure.

8. The apparatus according to claim 1, wherein the test material unit is an orthopedic surgery metal selected from the group consisting of aluminum, chromium, cobalt, molybdenum, nickel, vanadium, titanium and Ti6AI-4V.

9. The apparatus according to claim 1, wherein the test material unit is a dental implant material selected from the group consisting of titanium, zirconium, aluminum, and vanadium or a dental amalgam consisting essentially of a metal alloy mixture having mercury, silver, tin, copper, or combinations of two or more thereof.

10. The apparatus according to claim 1, wherein the top surface is smaller than the bottom surface and the top surface is fitted and secured in the concaved housing compartment of the holder.

11. A method of assessing skin reactivity to an implant material, prior to or after a subject undergoing implant surgery, to test tissue sensitivity of the subject to the implant material, comprising:
   applying the apparatus according to claim 1 on the skin of the subject, such that the test material unit of the apparatus makes the direct contact with the skin for the plurality of days; and
   determining a presence of skin reactivity based on one or more cutaneous reactions of the skin having the direct contact with the test material unit of the apparatus.

12. The method of claim 11, wherein the implant material is an orthopedic implant.

13. The method of claim 12, wherein the orthopedic implant is an orthopedic surgery metal selected from the group consisting of aluminum, chromium, cobalt, molybdenum, nickel, vanadium, titanium, and Ti6AI-4V.

14. The apparatus according to claim 1, wherein the test material unit is an orthopedic surgery metal alloy.

15. The apparatus according to claim 1, wherein the test material unit is an orthopedic surgery metal alloy of chromium, cobalt, or molybdenum.

16. The apparatus of claim 1, wherein the implant material is the metal alloy.

* * * * *